(12) United States Patent
Jacobs et al.

(10) Patent No.: US 12,288,614 B2
(45) Date of Patent: Apr. 29, 2025

(54) PLATFORM FOR HANDLING OF MEDICAL DEVICES ASSOCIATED WITH A MEDICAL DEVICE KIT

(71) Applicant: DEPUY SYNTHES PRODUCTS, INC., Raynham, MA (US)

(72) Inventors: Scott Jacobs, Honey Brook, PA (US); Urs Wigger, Feldbrunnen (CH)

(73) Assignee: DePuy Synthes Products, Inc., Raynham, MA (US)

( * ) Notice: Subject to any disclaimer, the term of this patent is extended or adjusted under 35 U.S.C. 154(b) by 308 days.

(21) Appl. No.: 16/719,202

(22) Filed: Dec. 18, 2019

(65) Prior Publication Data

US 2021/0193310 A1 Jun. 24, 2021

(51) Int. Cl.
*G16H 40/40* (2018.01)
*G06Q 10/087* (2023.01)
*G06T 11/00* (2006.01)

(52) U.S. Cl.
CPC .......... *G16H 40/40* (2018.01); *G06Q 10/087* (2013.01); *G06T 11/00* (2013.01)

(58) Field of Classification Search
None
See application file for complete search history.

(56) References Cited

U.S. PATENT DOCUMENTS

| | | | |
|---|---|---|---|
| 8,775,133 B2 | 7/2014 | Schroeder | |
| 9,066,755 B1 | 6/2015 | Jacobs et al. | |
| 9,129,054 B2 | 9/2015 | Nawana et al. | |
| 9,538,962 B1 | 1/2017 | Hannaford et al. | |
| 9,645,785 B1 | 5/2017 | Hannaford et al. | |
| 2016/0125603 A1 | 5/2016 | Tanji | |
| 2016/0171778 A1 | 6/2016 | Grossman et al. | |
| 2016/0180033 A1* | 6/2016 | Rosenberg | G06Q 10/087 705/2 |
| 2016/0287337 A1 | 10/2016 | Aram et al. | |
| 2016/0379504 A1* | 12/2016 | Bailey | G06F 16/50 434/219 |
| 2017/0039423 A1 | 2/2017 | Cork et al. | |
| 2017/0160549 A1 | 6/2017 | Badiali et al. | |
| 2018/0012413 A1 | 1/2018 | Jones et al. | |
| 2018/0012416 A1 | 1/2018 | Jones et al. | |
| 2018/0032130 A1 | 2/2018 | Meglan | |

(Continued)

FOREIGN PATENT DOCUMENTS

| | | |
|---|---|---|
| WO | 2017160889 A1 | 9/2017 |
| WO | 2018052966 A1 | 3/2018 |

*Primary Examiner* — Devin C Hein
(74) *Attorney, Agent, or Firm* — BakerHostetler

(57) ABSTRACT

Techniques for addressing various technical problems associated with managing medical devices and data related to medical devices, for instance medical implants in a graphics case or medical device kit, are described herein. One or more medical device handling applications can execute on a medical device computer system. Such a computer system can include one more computing devices, such as for example a client device and a server device, that can optionally communicate with each other to send and receive information associated with medical devices. The computer system can further include a wearable device and a server device that can optionally communicate with each other to send and receive information associated with medical devices and medical device kits.

18 Claims, 9 Drawing Sheets

(56) References Cited

U.S. PATENT DOCUMENTS

| | | | |
|---|---|---|---|
| 2018/0082480 A1* | 3/2018 | White | A61B 90/94 |
| 2018/0168741 A1 | 6/2018 | Swayze et al. | |
| 2018/0233222 A1 | 8/2018 | Daley et al. | |
| 2018/0310996 A1 | 11/2018 | Moctezuma et al. | |
| 2018/0311012 A1 | 11/2018 | Moctezuma et al. | |
| 2019/0198161 A1* | 6/2019 | Lee | G16H 40/20 |
| 2019/0321132 A1* | 10/2019 | Weir | A61B 50/33 |
| 2019/0380792 A1* | 12/2019 | Poltaretskyi | G06K 9/6261 |
| 2020/0253683 A1* | 8/2020 | Amanatullah | G16H 20/40 |

* cited by examiner

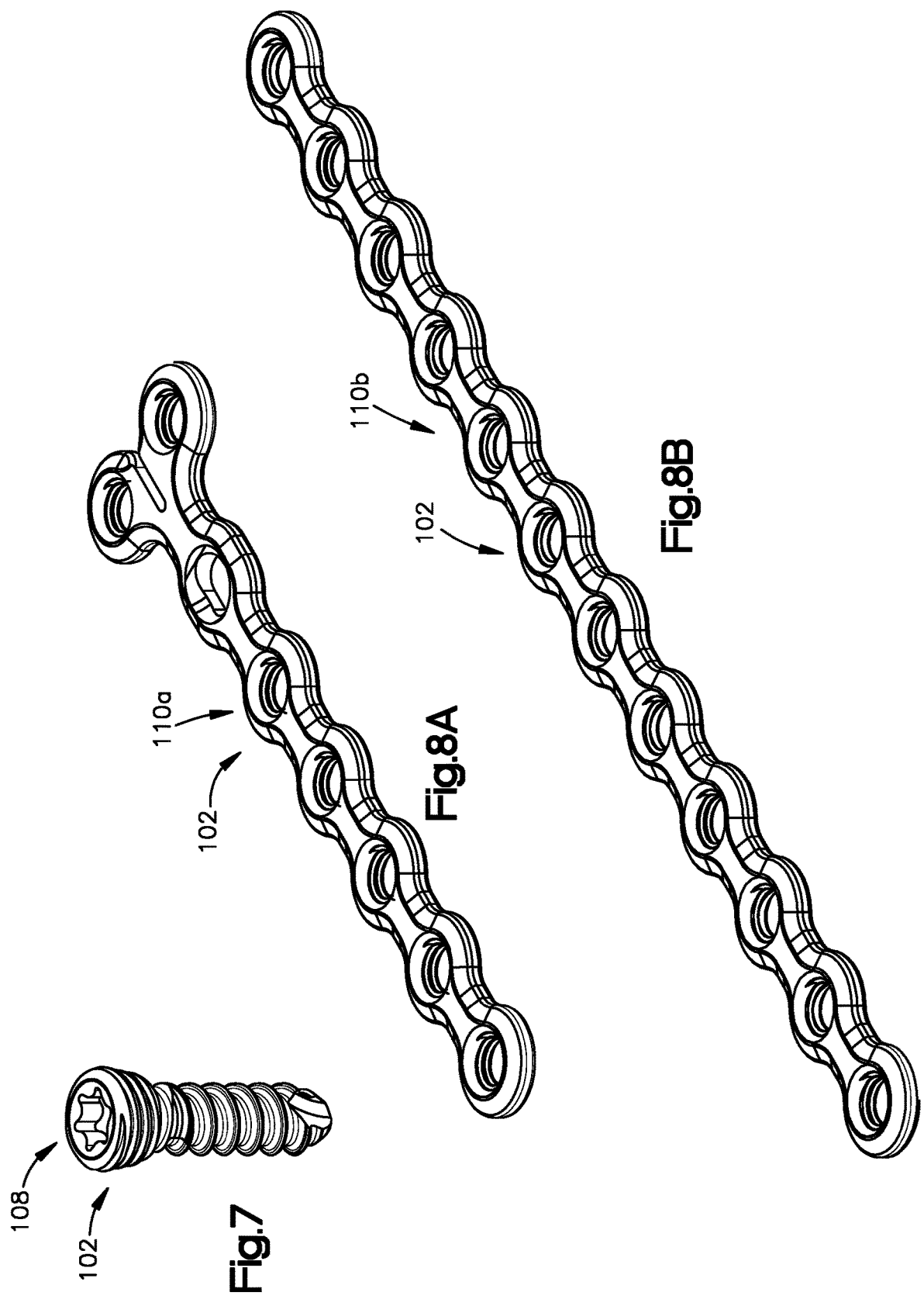

PLATFORM FOR HANDLING OF MEDICAL DEVICES ASSOCIATED WITH A MEDICAL DEVICE KIT

BACKGROUND

Augmented reality generally refers to an area of technology in which a perception of a real-world environment is augmented or supplemented by computer-generated information, such as by inserting computer-generated graphics (e.g., one or more virtual objects) into a view of a physical space. Computer-generated information that can augment reality may include, for example, sound, video, graphics, or GPS data. In an example, images and/or video of a physical space, such as a physical object, may be captured using a camera. The captured images may then be augmented, such as by inserting virtual objects into the image to overlay various locations within the image. In another example, a view of a physical space may be augmented by overlaying one or more virtual objects over a view of a physical space itself, such as by displaying the virtual objects on an eyeglass or other translucent display.

Medical devices, such as medical implants, are often loaded into a case for a particular medical procedure. Controlling and tracking the devices and information related to the devices can be a technical challenge, as the devices can be complex and errors in loading the cases or implementing the devices within the cases can cause significant problems before, during, and after a given medical procedure. Furthermore, managing the data associated with a given case can cause latency issues, among others, which are unacceptable in the time-sensitive environments in which the medical devices are utilized.

SUMMARY

Techniques for addressing various technical problems associated with managing medical devices and data related to medical devices, for instance medical implants and/or medical instruments, in a graphics case or medical device kit, are described herein. In one embodiment, one or more medical device handling applications can execute on a medical device computer system. The applications can be an augmented reality application, a virtual reality application, a mixed reality application, an extended reality application, or any combination thereof. Such a computer system can include one more computing devices, such as for example a client device and a server device, that can optionally communicate with each other to send and receive information associated with medical devices. The computer system can further include a wearable device and a server device, that can optionally communicate with each other to send and receive information associated with medical devices and medical device kits.

In an example aspect, a medical device computer system includes a processor and a display configured to display virtual objects along with a view of a medical device kit. The medical device kit image can include a plurality of storage locations within the medical device kit. The plurality of storage locations can be configured to store a plurality of medical devices. The display can be configured to be worn by a user, for instance as eyeglasses or goggles. For example, the display can include translucent glass, such that the medical device kit can be viewed through the translucent glass, and virtual objects can be displayed on the translucent glass so as to generate augmented views of medical device kits and medical devices. Additionally, or alternatively, the display can include a screen, such that the medical device kit can be viewed on the screen, and virtual objects can be displayed on the screen so as to generate augmented views of medical device kits and medical devices. The computer system can further include an image sensor in communication with the processor. The image sensor can be configured to detect one or more physical characteristics of the medical device kit. The computer system can be configured to determine a rule set corresponding to at least one of the medical device kit and the plurality of medical devices configured to be stored in the medical device kit. The computer system can compare the one or more physical characteristics of the at least one of the medical device kit and the plurality of medical devices to the rule set. Based on the comparison of the one or more physical characteristics of the medical device kit to the rule set, the computer system can select a first virtual object to augment the view of the medical device kit. The computer system can insert the first virtual object into the view of the medical device kit so as to generate a first augmented view of the medical device kit.

The foregoing summarizes only a few aspects of the present disclosure and is not intended to be reflective of the full scope of the present disclosure. Additional features and advantages of the disclosure are set forth in the following description, may be apparent from the description, or may be learned by practicing the invention. Moreover, both the foregoing summary and following detailed description are exemplary and explanatory and are intended to provide further explanation of the disclosure.

BRIEF DESCRIPTION OF THE DRAWINGS

The foregoing summary, as well as the following detailed description of example embodiments of the present disclosure, will be better understood when read in conjunction with the appended drawings. For the purposes of illustrating the example embodiments of the present disclosure, references to the drawings are made. It should be understood, however, that the application is not limited to the precise arrangements and instrumentalities shown. In the drawings:

FIG. 7 is a perspective view of a medical screw that can be augmented in accordance with an example embodiment;

FIGS. 8A-B are perspective views of respective medical plates that can be augmented in accordance with an example embodiment.

DETAILED DESCRIPTION OF ILLUSTRATIVE EMBODIMENTS

Various techniques for augmentation of physical objects, for instance medical devices or medical device kits, are described herein.

Figure 1:
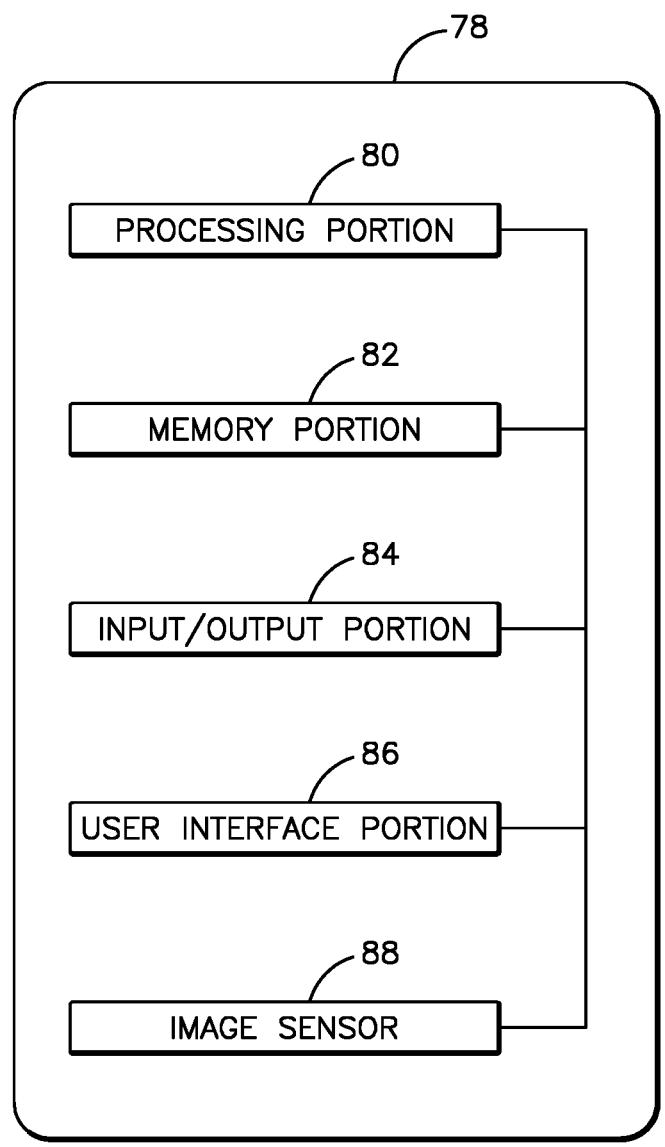
FIG. 1 is a block diagram of an example computing device for use in accordance with the present disclosure.

Referring to FIG. 1, a suitable computing device such as an example computing device 78, can be configured to host a medical device handling application. The medical device handling application can be an augmented reality application, a virtual reality application, a mixed reality application, an extended reality application, or any combination thereof. A wearable device 90 (shown in FIG. 2), such as a head-mounted display, can include the computing device 78. In an example, the head-mounted display can be eyeglasses or goggles such as those used in augmented reality, virtual reality, mixed reality, or extended reality. Alternatively, or additionally, the wearable device 90 can be in communication with the computing device 78, for instance over a network or a direct peer-to-peer link. The medical device handling application can be a program, such as software or hardware or a combination of both, that can be run on one or more suitable computing devices. It will be appreciated that the embodiments described herein can be applied to augment or virtually supplement any medical device or storage object, for instance any medical implant, instrument, or kit for any medical procedure. In this regard, reference below to the medical device handling application can be further construed as an application that can assist in the handling of devices associated with a medical device kit, such as the loading or assembly of devices within the medical device kit, and can additionally assist in the management of medical devices and data associated with a medical device before and after the medical devises are used on a patient. It will be understood that the computing device 78 can include any appropriate device, examples of which include a desktop computing device, a server computing device, or a portable computing device, such as a laptop, tablet, or smart phone.

In an example configuration, the computing device 78 includes a processing portion 80, a memory portion 82, an input/output portion 84, a user interface (UI) portion 86, and a sensor portion or image sensor 88. It is emphasized that the block diagram depiction of the computing device 78 is exemplary and not intended to imply a specific implementation and/or configuration. The processing portion 80, memory portion 82, input/output portion 84, user interface portion 86, and image sensor 88 can be coupled together to allow communications therebetween. As should be appreciated, any of the above components may be distributed across one or more separate devices and/or locations. For example, the wearable device 90 can include any or all of the processor portion 80, memory portion 82, input/output portion 84, user interface portion 86, and the image sensor 88.

In various embodiments, the input/output portion 84 includes a receiver of the computing device 78, a transmitter of the computing device 78, or a combination thereof. The input/output portion 84 is capable of receiving and/or providing information pertaining to a communications network such as, for example, the Internet. As should be appreciated, transmit and receive functionality may also be provided by one or more devices external to the computing device 78.

The processing portion 80 may include one or more processors. Depending upon the exact configuration and type of processor, the memory portion 82 can be volatile (such as some types of RAM), non-volatile (such as ROM, flash memory, hard disk drive, etc.), or a combination thereof. The computing device 78 can include additional storage (e.g., removable storage and/or non-removable storage) including, but not limited to, tape, flash memory, smart cards, CD-ROM, digital versatile disks (DVD) or other optical storage, magnetic cassettes, magnetic tape, magnetic disk storage or other magnetic storage devices, universal serial bus (USB) compatible memory, or any other medium which can be used to store information and which can be accessed by the computing device 78.

The computing device 78, and in some examples the wearable device 90, also can contain the user interface portion 86 allowing a user to communicate with the computing device 78. The user interface 86 can include inputs that provide the ability to control the computing device 78, via, for example, buttons, soft keys, a mouse, voice actuated controls, a touch screen, movement of the computing device 78, visual cues (e.g., moving a hand in front of a camera on the computing device 78), audio cues, or the like. The user interface portion may also include, for example, a scanner for scanning of information such as bar codes. The user interface portion 86 can provide outputs, including visual information (e.g., via a display), audio information (e.g., via speaker), mechanically (e.g., via a vibrating mechanism), or a combination thereof. In various configurations, the user interface portion 86 can include a display, a touch screen, a keyboard, a mouse, an accelerometer, a motion detector, a speaker, a microphone, a camera, a tilt sensor, or any combination thereof. The user interface portion 86 can further include any suitable device for inputting biometric information, such as, for example, fingerprint information, retinal information, voice information, and/or facial characteristic information. Thus, a medical device computer system including, for example, computing device 78 can include a processor, a display coupled to the processor, and a memory in communication with the processor. The display can be translucent, or the display can include translucent glass, so that a user can view real-world objects through the display. For example, the display can be configured to be worn by a user, so that user can view a medical device kit and/or medical device through the display. Further, virtual object can be configured to be displayed on the translucent glass, so as to generate an augmented views of medical device kits or medical devices. In alternative embodiments, the display can be a screen that is configured to display real-world objects and virtual objects so as to generate augmented views that include both the real-world objects and virtual objects.

The memory can have stored therein instructions that, upon execution by the processor, cause the computer system to perform operations, such as the operations described below. The display can be configured to display virtual objects or images, such as described herein with reference to FIG. 6B. As used herein, the term computer system can refer to a system that includes one or more computing devices 78. For instance, the computer system can include one or more server computing devices that communicate with one or more client computing devices. By way of further example, the computer system can include one or more wearable devices that communicate with one or more server computing devices.

The computing device 78, and thus the wearable device 90, can also contain the sensor portion 88, which can include one or more cameras, sensors, or other data capture components. The sensor portion or image sensor 88 can detect physical images when the physical image is within a field of view of the image sensor 88. The image sensor 88 can be in communication with the display of the wearable device 90. In particular, the image sensor 88 can be configured to detect one or more physical characteristics of medical device kits or medical devices.

Figure 2:
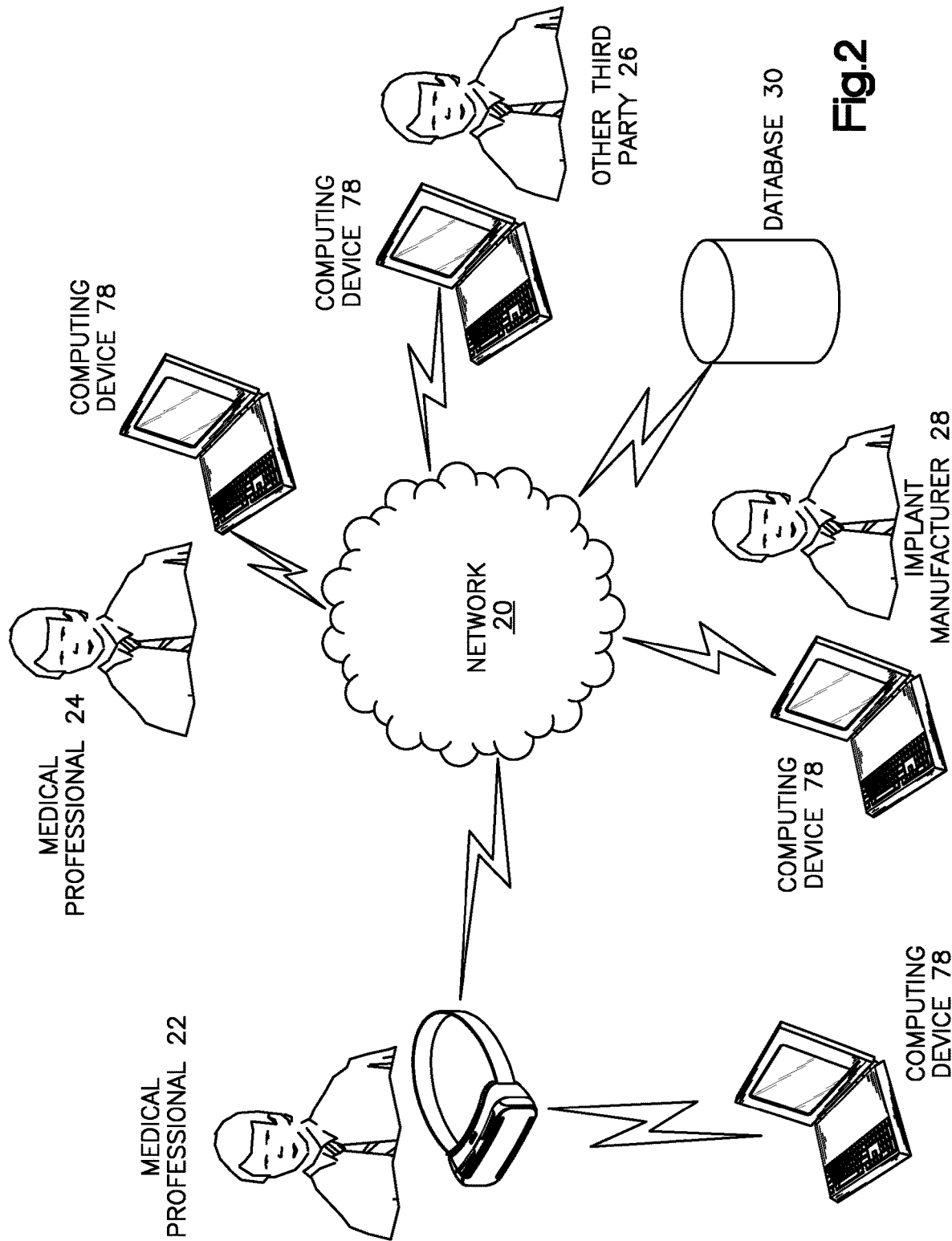
FIG. 2 is an example augmented reality platform for use in accordance with the present disclosure.

FIG. 2 depicts one example of a suitable communication architecture or platform in which the medical device handling application can be utilized, it being appreciated that numerous suitable alternative communication architectures are envisioned. Once one or more medical device handling applications have been installed onto a computer system including, for example, the computing device 78 and/or the wearable device 90 such as described above, information may be transferred between other computing devices 78 on a common network 20, such as, for example, the Internet. Example computing devices 78 include, without limitation, desktops, laptops, mobile phones, tablet computers, or the like.

Figure 3:
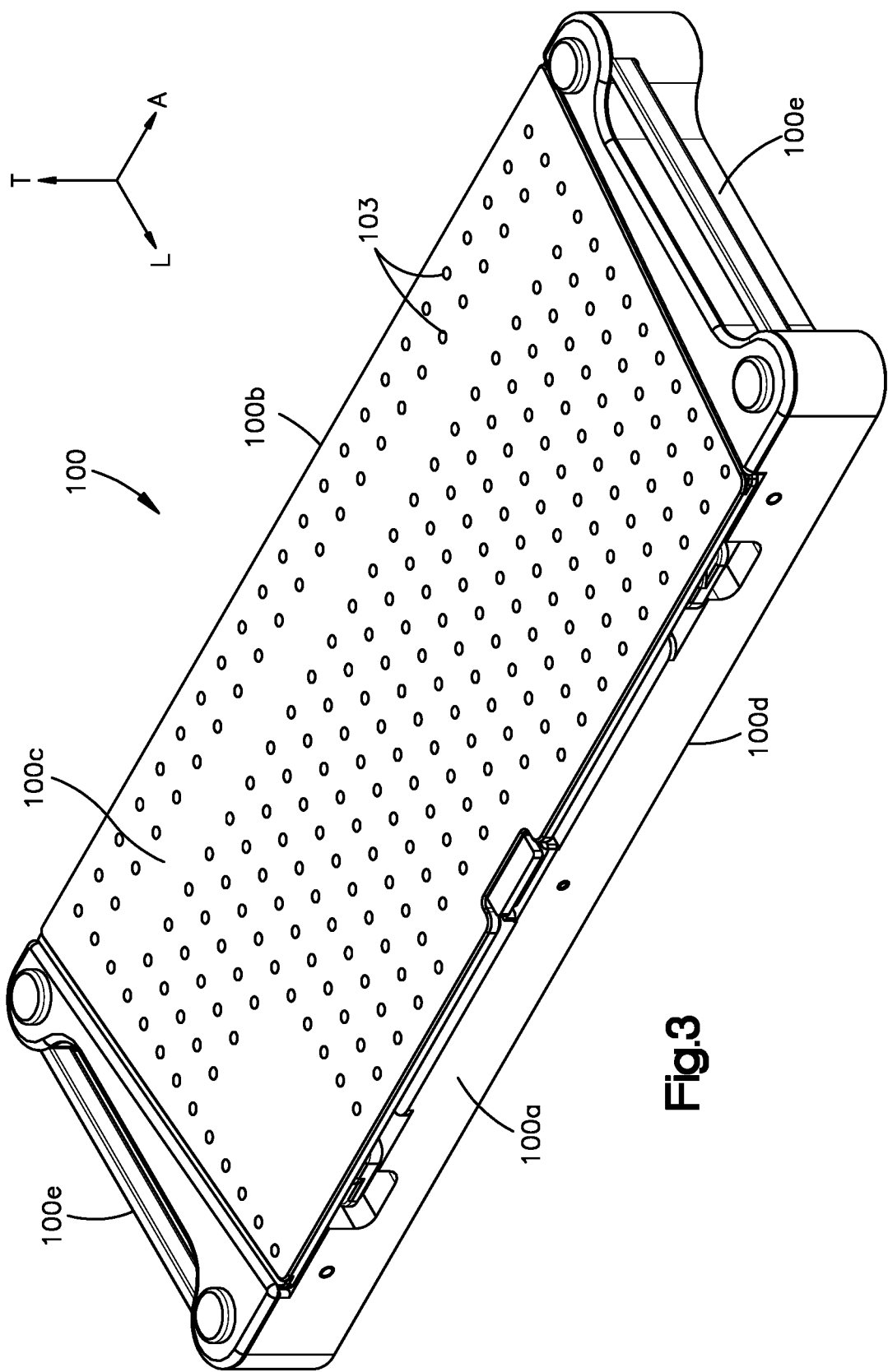
FIG. 3 is a perspective view of an example medical device kit.
Figure 4:
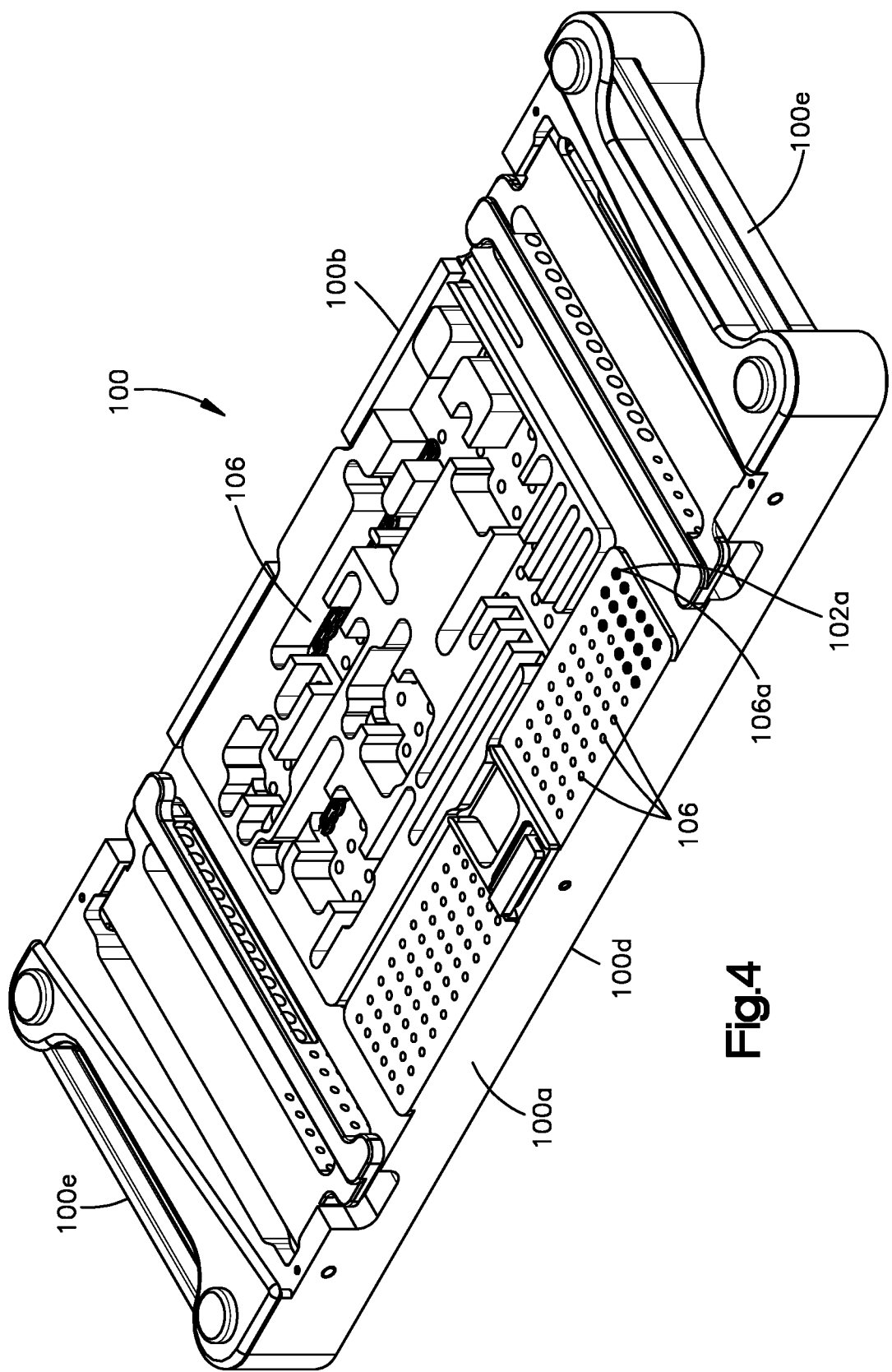
FIG. 4 is a perspective view of the medical device kit shown in FIG. 3, wherein a cover is removed to shows various medical devices stored at various storage locations within the medical device kit.
Figure 5:
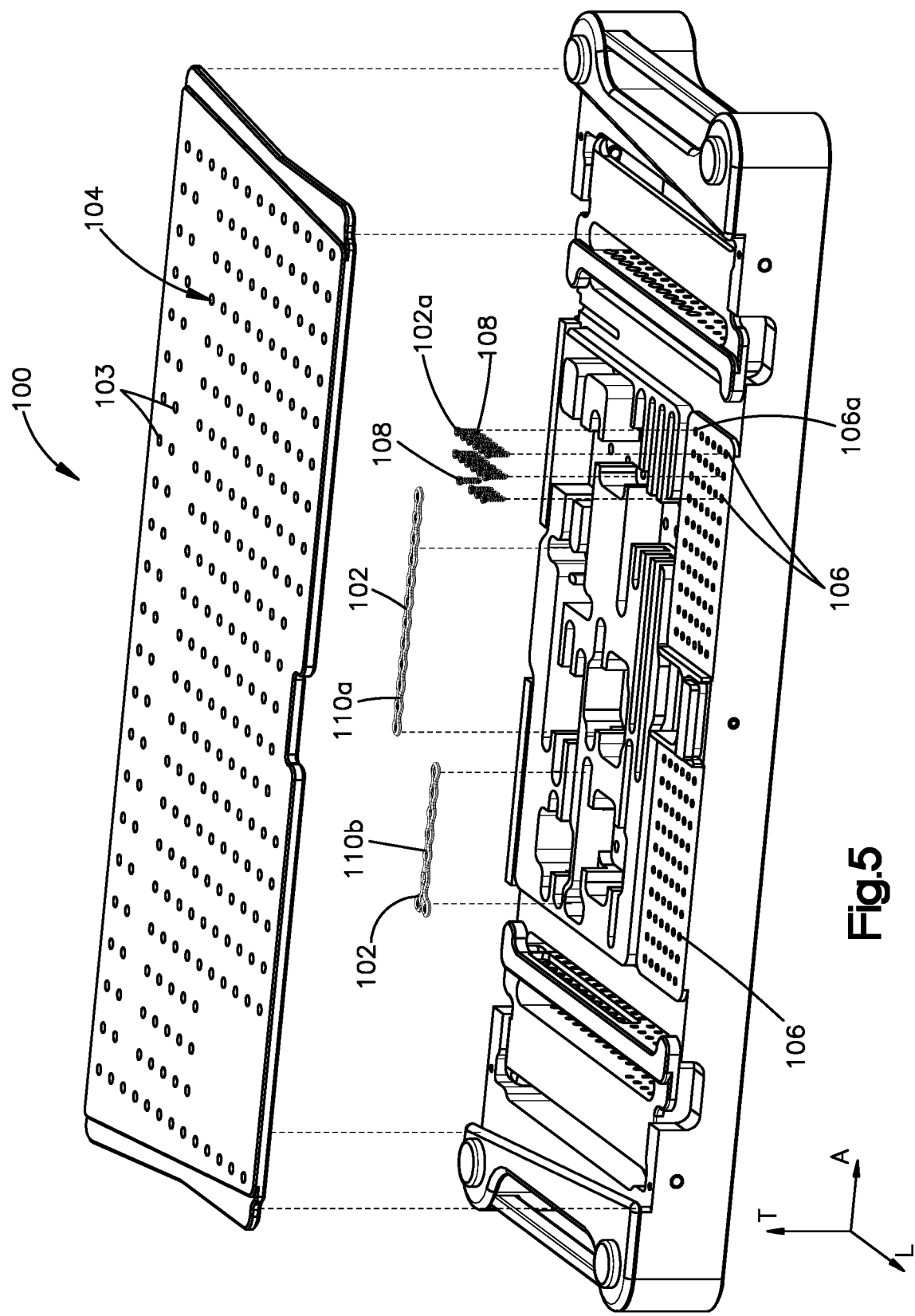
FIG. 5 is an exploded view of the storage object shown in FIG. 3, wherein the medical devices are aligned with their respective storage locations along a transverse direction.

In an example configuration, referring also to FIGS. 3-5, a first user or medical professional 22, such as a technician or nurse, may store medical devices 102 within a storage object or medical device kit 100, so as to load or assemble the medical device kit 100. Rule sets can be determined for a given medical device kit, such as the example medical device kit 100. Further, a rule set can be determined that corresponds to a plurality of medical devices 102 configured to be stored in the medical device kit 100. In an example configuration, the medical device kit 100 is used for a particular medical procedure or a particular subset of medical procedures. Each medical procedure can require particular medical devices 102, and a rule set for the medical procedure can determine which devices are loaded or assembled into the medical device kit 100. Thus, a rule set can correspond to a plurality of medical devices 102 that are configured to be stored in the medical device kit 100. In an example, a machine-readable code, for instance a QR code, is scanned on the medical device kit 100. The machine-readable code can identify the medical device kit 100, and thus can identify at least one rule set associated with the medical device kit 100, and the medical devices 102 that should be loaded into the medical device kit 100.

The at least one rule set can include rules pertaining to the handling of the medical devices 102 of the medical device kit 100, such as instructions to guide the user in interacting with the medical devices 102. For example, the at least one rule set can include rules pertaining to how to populate the medical devices 102 in the medical device kit 100. Additionally, or alternatively, the at least one rule set can include rules pertaining to replenishment of the medical devices 102 of the medical device kit 100 in inventory. Additionally, or alternatively, the at least one rule set can include rules pertaining to cleanliness of the medical devices 102 of the medical device kit 100. Additionally, or alternatively, the at least one rule set can include rules pertaining to physical abnormalities with the medical devices 102, such as defects with, or damage to, the medical devices 102. Thus, the at least one rule set can include rules pertaining to at least one, up to all, of (i) population of the medical device kit 100, (ii) replenishment of the medical devices 102 in inventory, (iii) cleanliness of the medical devices 102, and (iv) physical abnormalities of the medical devices 102.

The computing device 78 can retrieve the at least one rule set based on the machine-readable code. The computing device 78 can send the machine-readable code to a database 30 to retrieve the rule set. It will be understood that the medical device kit 100, and thus the at least one rule set associated with the medical device kit 100, may be identified in an alternative manner. For example, a user or health care professional could manually enter a code that identifies the medical device kit 100. The at least one rule set that is associated with the medical device kit 100 and the medical devices 102 can be used to populate virtual objects associated with a given medical device kit or medical device. The at least one rule set that is associated with the medical device kit 100 can be used to gather data related to the medical device kit 100. In particular, the at least one rule set that is associated with the medical device kit 100 can be used to gather data related to one or more medical devices 102 associated with the medical device kit 100.

Figure 6A:
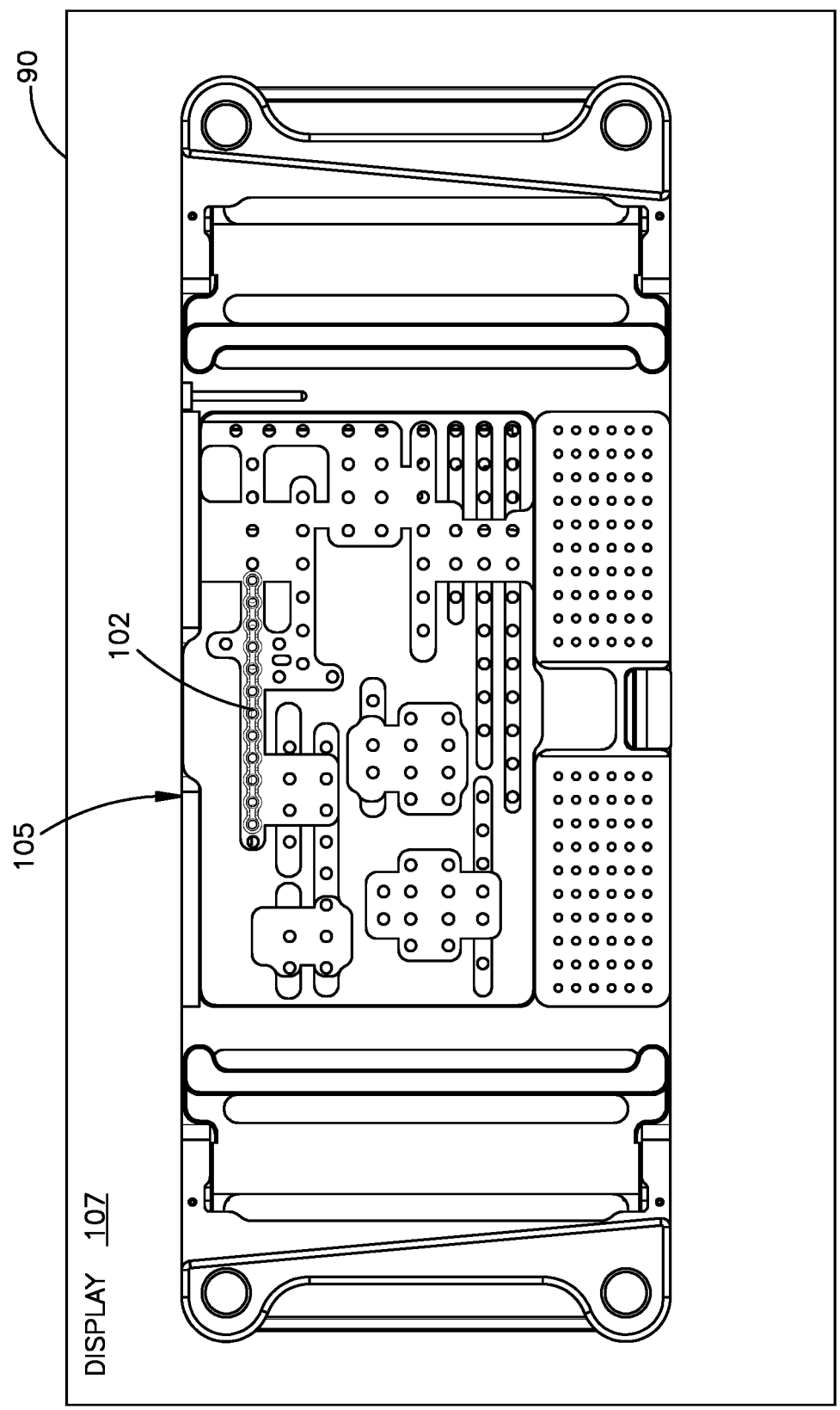
FIG. 6A depicts a physical view of the medical device kit through a translucent display of a wearable device.
Figure 6B:
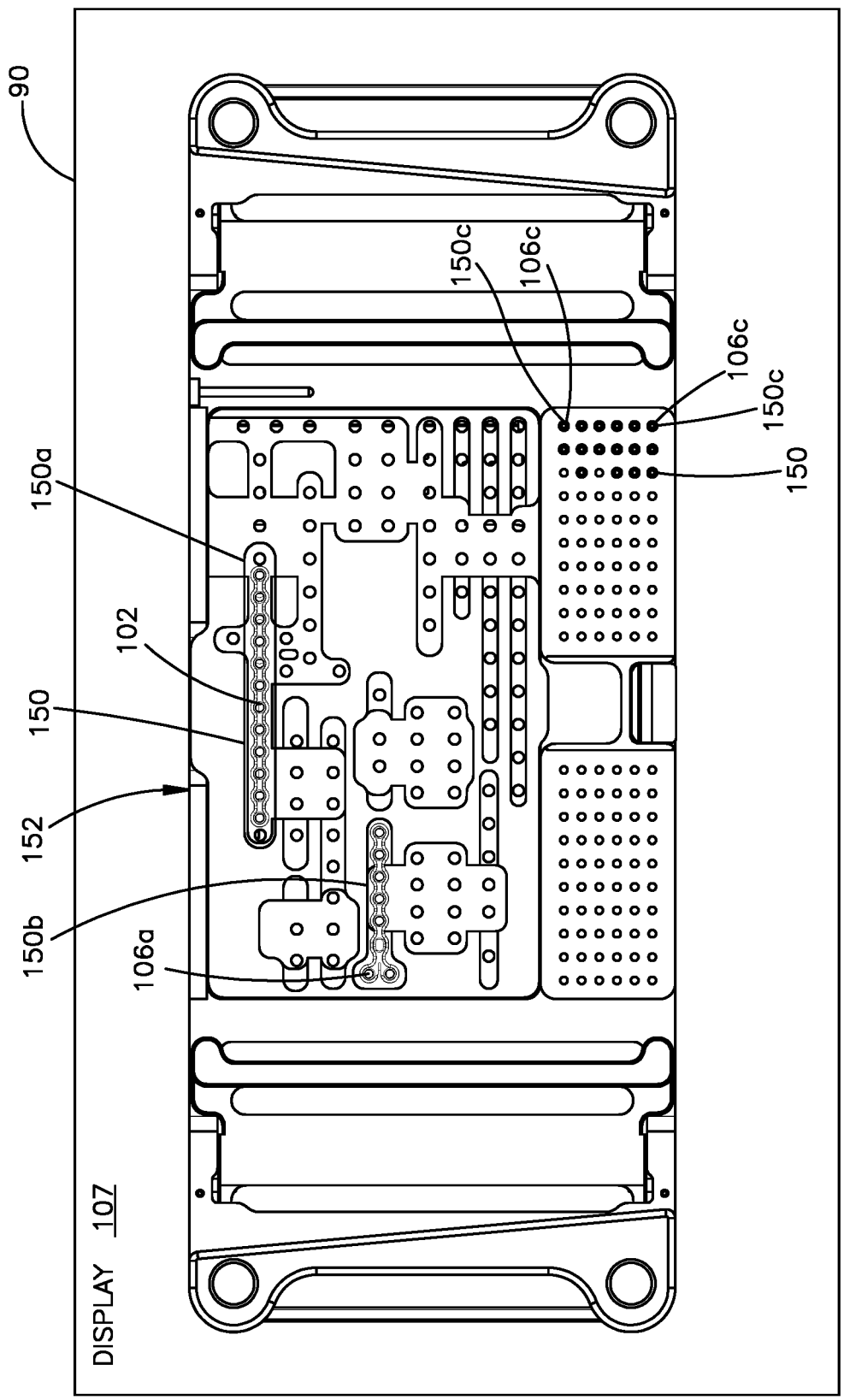
FIG. 6B depicts an augmented view of the medical device kit shown in FIG. 6A, shown through the translucent display of the wearable device, wherein the augmented view includes at least one virtual object superimposed on the physical view shown in FIG. 6A.

Referring also to FIGS. 6A and 6B, by way of example, the medical professional 22 can view the medical device kit 100 through the wearable device 90, in particular through a translucent display or glass 107 of the wearable device 90. The image sensor 88 of the wearable device 90 can detect an actual or physical image 105 that includes the medical device kit 100 when the medical device kit 100 is within a field of view of the image sensor 88. Based on the at least one rule set that is associated with the medical device kit 100, the computing device 78 can determine which medical devices 102 should be loaded into the medical device kit. Further, the computing device 78 can identify storage locations 106 within the medical device kit 100. In particular, the image sensor 88 can detect storage locations 106 within the medical device kit 100. The wearable device 90 can provide an indication to the medical professional 22 so that the medical professional 22 is informed of which medical devices should be stored at which locations 106. For example, referring to FIG. 6B, the wearable device 90 can overlay or superimpose a virtual object 150 over a respective physical location of the medical device kit 100. The virtual object 150 may identify the medical device 102 that should be stored at the location at which the virtual object is overlaid. Alternatively, the wearable device 90 can display a virtual object adjacent to the physical location of the medical device kit 100. For example, the wearable device 90 could display a virtual image (e.g., hologram) of the medical device kit 100 next to the actual view of the medical device kit 100 so that a user can compare the two.

The virtual objects 150 can include computer generated graphics that represent or depict various locations within the medical device kit 100, various medical devices 102, or other items or objects. The virtual objects 150 can include graphics that represent physical objects that are used in a particular medical procedure. For example, the virtual objects can include holograms of physical objects such as medical devices. The virtual objects can include graphics that represent physical locations within the medical device kit 100. Additionally, or alternatively, the virtual objects 150 can include various colors, text, or graphics that convey data or information associated with an actual object. In some examples, the virtual objects 150 can include an indicia, such a colored border, that highlights an object or physical location within the medical device kit 100.

When one of the medical devices 102 are stored, the image sensor 88, and thus the computing device 78, can detect that the associated storage location is no longer vacant. In response to identifying that the location is no longer vacant, the wearable device 90 can remove the virtual object, for instance a graphic, from the display that indicated which medical device should be stored at the given location. The image sensor 88 can also detect and identify medical devices. Therefore, if the wrong medical device is loaded at a given location, the wearable device 90 can provide an indication, for instance a graphic over the given location or an audible tone, that indicates that an improper medical device was loaded at the given location. The wearable device 90 can determine that the wrong medical device was stored at a given location based on the rule set associated with the storage object 100 and the medical device. Similarly, when the correct medical device is loaded at a particular location, the wearable device 90 can provide an indication, for instance a graphic over the location or an audible tone, that indicates that the appropriate medical device was loaded at the appropriate location. The wearable device 90 can determine that the correct medical device was stored at a given location based on the rule set associated with the storage object 100 and the medical device. In another example configuration, the medical professional 22 can scan or manually enter identifying information of a given medical device into the computing device 78, and the wearable device can provide the indications described above to direct the medical professional in the appropriate storage of the medical device.

During an assembly process, the computing device 78 can determine at least one, for instance all, medical devices that are missing from the medical device kit 100. This determination can be based on the at least one rule set that pertains to populating the medical devices 102 in the medical device kit 100. For instance, the image sensor 88 can identity vacant storage locations within the medical device kit 100, and can determine which medical devices should be stored in the vacant locations. The computing device 78 can determine a location of a missing medical device in inventory. By way of example, the image sensor 88 can send an identifier of the medical device 102 to the database 30 or to another computing device 78. Based on the identifier, the database 30 can locate the medical device in inventory. Similarly, another third party 26, such as a medical sales representative or hospital distribution center, can receive the identifier of the missing medical device from the wearable device 90 via the network 20, and can locate the missing medical device. For instance, inventory information can be stored in one or more databases. The database 30 or other computing device 78 can send a message to the wearable device 90 that informs the wearable device 90 of the location of the missing medical device. In response, the wearable device 90 can generate a virtual object or image. The virtual image can include instructions, for instance text or graphics, which guide the medical professional 22 in retrieving the missing medical device from inventory, cleaning the medical device, assembling or disassembling the medical device, inspecting the medical device, calibrating the medical device, replacing the medical device, or any combination of such instructions. In an example, the virtual object that includes instructions can be overlaid or superimposed over the physical image, in particular the physical location, that corresponds to the missing medical device.

The computing device 78 can additionally, or alternatively, assist in inventory control of the medical devices of the medical device kit 100. In an example, the computing device 78 can determine whether at least one, for instance all, medical devices of the medical device kit 100 are in stock in inventory. This determination can be based on at least one rule set that pertains to replenishment in inventory of the medical devices 102 of the medical device kit 100. For instance, when the image sensor 88 identifies vacant storage locations within the medical device kit 100, the image sensor 88 can send an identifier of the missing medical device 102 to the database 30 or to another computing device 78. Based on the identifier, the database 30 determine whether the medical device is in stock in inventory. Similarly, another third party 26, such as a medical sales representative or hospital distribution center, can receive the identifier of the missing medical device from the wearable device 90 via the network 20, and can determine whether the missing medical device is in stock in inventory. The database 30 or other computing device 78 can send a message to the wearable device 90 that informs the wearable device 90 that the missing medical device is not in stock in inventory. In response, the wearable device 90 can generate a virtual object or image that alerts the medical professional 22 that the medical device is not in stock in inventory. In some examples, the virtual image can include instructions, for instance text or graphics, which guide the medical professional 22 in reordering the missing medical device. The virtual object that includes instructions can be overlaid or superimposed over the physical image, such as the physical location, that corresponds to the missing medical device. In other examples, the computing device 78 can automatically reorder the missing medical device.

Thus, as further described below, the medical device 102 and information associated with the medical device 102 can be tracked and managed. Further, the medical device kit 100 can be properly assembled, thereby limiting or eliminating costly human errors that can be common to assembling a medical device kit, and thereby decreasing the latency in assembling a medical device kit. The information that is rendered or received by the wearable device 90 can be transmitted to other computing devices 78, such as between mobile devices for example, via the network 20. For instance, a second medical professional 24, an implant manufacturer 28, or another third party 26 can receive the information associated with the medical device 102 via the network 20.

In an example embodiment, using the medical device handling application as described herein, rule sets can be retrieved from the database 30. The rule sets can correspond to the plurality of medical devices configured to be stored in the medical device kit 100. Thus, the computing device 78 can determine a rule set corresponding to the plurality of medical devices configured to be stored in the medical device kit 100. Alternatively, or additionally, the rule sets can be stored in memory local to the wearable device 90.

Referring to FIGS. 3-5, while the medical device kit 100 is illustrated as a graphic case, it will be appreciated that medical devices can be managed that are stored within any type of unit as desired. Thus, it will be understood that the medical device kit 100 can be implemented by, for example, a graphic case, a screw rack, a removable module that can be stored within a graphic case, or the like, or any appropriate combination thereof.

The computing devices 78 and the database 30 depicted in FIG. 2 can be operated in whole or in part by, for example, a medical device manufacturing company, a hospital, a healthcare professional, another third party, or by any combination of any of the above entities. As should be appreciated, each of the parties set forth above and/or other relevant parties may operate any number of respective computers and may communicate internally and externally using any number of networks including, for example, wide area networks (WAN's) such as the Internet or local area networks (LAN's). Database 30 may be used, for example, to store information and rule sets for medical devices and medical device kits that are used for various medical procedures. Database 30 may also be used, for example, to store information obtained from parties such as healthcare professionals and medical device manufacturers.

With reference to FIGS. 3 to 5, an example medical device kit 100 can define a front end 100a and an opposed rear end 100b that is spaced from the front end 100a along a longitudinal direction L, a top end 100c and an opposed bottom end 100d that is spaced from the top end 100c along a transverse direction T that is substantially perpendicular to the longitudinal direction L, and opposed sides 100e that are spaced from each other along a lateral direction A that is perpendicular to both the transverse direction T and the longitudinal direction L. Unless otherwise indicated herein, the terms "lateral," "longitudinal," and "transverse" are used to describe the orthogonal directional components of various components. The terms "inboard" and "inner," and "outboard" and "outer" and like terms when used with respect to a specified directional component are intended to refer to directions along the directional component toward and away from the center of the apparatus being described.

As will be appreciated from the description below, the top end 100c can define a cover 104 that can be removed or opened so that medical devices 102 can be placed in the medical device kit 100 or removed from the medical device kit 100. It will further be appreciated that the medical device kit 100 can alternatively be accessed so as to place medical devices within the medical device kit 100 or to remove medical devices from the medical device kit 100. As illustrated, the cover 104 can include holes 103 that allow steam to pass through the cover 104 so as to sterilize the medical devices 102 that are stored within the storage object 100. It will be appreciated that the holes 103 can be alternatively placed as desired, for instance at the bottom end 100d. Referring in particular to FIG. 5, in accordance with the illustrated example, medical devices 102 can be aligned with respective storage locations 106 along the transverse direction T so that the storage locations 106 can receive the respective medical devices 102 along the transverse direction T. It should be appreciated that while the longitudinal and lateral directions L and A are illustrated as extending along a horizontal plane, and that the transverse direction T is illustrated as extending along a vertical plane, the planes that encompass the various directions may differ during use, depending, for instance, on the orientation of the various components.

It will be understood that the medical devices 102 can include any medical device as desired. For instance, referring also to FIGS. 7-8B, the medical devices 102 that can be stored within the storage object 100, and thus can be augmented by the medical device handling application, can include, for example, medical screws 108 and medical bone plates 110a and 110b. The medical devices 102 can include other types of medical implants. For example, the medical devices 102 can include implants such as hip implants, knee implants, shoulder implants, intervertebral implants, pedicle screws, rods, intramedullary nails, and so on. The medical devices 102 can be configured to be implanted within a given patient. The medical devices 102 can additionally or alternatively be configured to be directly or indirectly attached and/or fixated to the patient. For example, the medical devices 102 can include external fixators such as frames and bridges that are configured to stabilize bone fractures. The medical devices 102 may also include any other type of device that can be used for medical purposes in connection with one or more patients. For example, the medical devices 102 can include medical instruments or instrument sets such as, for example, forceps, distractors, retractors, aiming guides for implantation of bone anchors, pedicle screw insertion tools, and so on.

The medical devices 102 can be sterile medical devices or nonsterile medical devices. The medical devices 102 can include medical implants that can be fabricated from any biocompatible, implantable material as desired, including metals such as titanium, titanium alloy such as Ti-6Al-7Nb, or stainless steel, polymers such as polyetheretherketone (PEEK), reinforced plastics, and the like. In some cases, the medical devices 102 may be directly marked with corresponding medical device identifiers. For example, in some cases, a particular medical device 102 may have a corresponding medical device identifier etched onto its surface. In such cases, the image sensor 88 can detect the medical device identifier so as to identify the medical device. The medical device handling application, in particular the image sensor 88, can also be used to identify and manage medical devices 102 that are not directly marked. For instance, the image sensor 88 can detect one or more physical characteristics of medical devices, for instance unmarked medical devices, so as to identify the medical devices. The physical characteristics can include characteristics such as size, shape, color, markings, and so on. The markings can include a unique device identification, a text part number, instructions, orientation markings, device description, and so on.

Referring in particular to FIG. 6A, the computing device 78 can include the image sensor 88 in communication with the display 107 of the wearable device 90. The image sensor 88 can be configured to detect the actual or physical image 105 of the medical device kit 100. The physical image 105 can include the medical device kit 100 when the medical device kit is within a field of view of the image sensor 88. In an example configuration, the image sensor 88 can identify a physical object, for instance the medical device kit 100 or the medical device 102, or any other real-world three-dimensional object. An example physical object view is a view of the physical object, such as an image or video of the physical object, or a view of the actual physical object itself, for example as may be seen through eyeglasses and/or the translucent display 107 through which the physical object is viewed. As will also be described in detail below, virtual objects 150 may be generated and inserted into the physical object view, for instance a view of the medical device kit 100, so as to create an augmented view 152 of the physical object, for example the medical device kit 100 or the medical devices 102. In some examples, the selected virtual objects 150 may be inserted into one or more images and or video of the physical object. In other examples, the virtual objects 150 may be displayed via eyeglasses and/or a translucent display through which the physical object is viewed.

In an example, at least one medical device kit image representative of the medical device kit 100 is captured, such as via one or more cameras, image sensors, or other data capture components. For instance, the image can be captured by one or more of the computing devices 78, one or more cameras that are positionally fixed within a medical facility, one or more cameras that is movable within the facility such as on a robot, or any combination of the one or more computing devices 78, the one or more fixed cameras, and the one or more mobile cameras. The at least one medical device kit image can be obtained at a single physical location of the medical device kit or at multiple different locations in which the medical device kit is moved. The at least one medical device kit image can include one or more images, image data, and/or other data that identifies attributes or physical characteristics of the medical device kit 100. Similarly, a medical device image of the medical device 102 can be captured, such as via or one or more cameras, image sensors, or other data capture components. The medical device image can include one or more images, image data, and/or other data that identifies attributes or physical characteristics of the medical device 102. The image data can be analyzed, for example by one or more computer-executed data analysis processes, to determine physical characteristics of the medical device kit 100 or medical device 102. For example, the detected image of the medical device kit 100 or medical device 102 can be analyzed by object recognition components of one of the computing devices 78. The object recognition components can analyze physical or image data to recognize various objects, or the absence of various objects, such as various medical devices, within the medical device kit 100. Similarly, the object recognition components can analyze physical or image data to recognize various characteristics, for instance flaws or defects, of medical devices 102.

Figure 9:
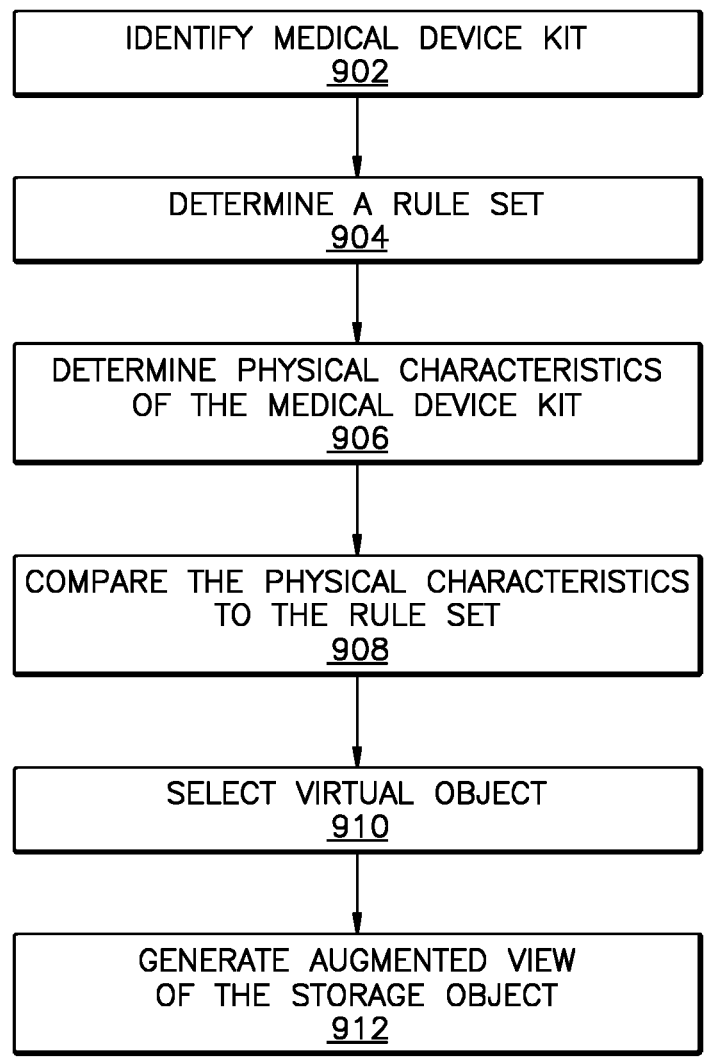
FIG. 9 is a flowchart of a method for managing a medical device kit in accordance with an example embodiment.

Referring to FIG. 9, the steps depicted in FIG. 9 can be performed by one or more medical device handling applications, which can be installed on a computer system that includes one or computing devices such as a desktop, laptop, mobile phone, a wearable device, or a tablet computer. Components or computing devices within the computer system can communicate with each other via an architecture as depicted in FIG. 2 or an alternatively configured architecture as desired. In some cases, different computers and/or computing devices within a computer system may perform various different steps depicted in FIG. 9.

With continuing reference to FIG. 9, a medical device kit, for instance the medical device kit 100, is identified at 902. In an example, the medical device kit 100 can include an identifier, such as a serial number for instance. The identifier can include a code, for instance a QR code, that can be scanned by the image sensor 88, or the identifier can be alternatively entered into the medical device handling application. The identifier of the medical device kit 100 can be associated with a particular medical procedure corresponding to a particular patient. Additionally or alternatively, a particular medical procedure, such as a procedure code or patient name for the procedure, can be entered or scanned into the medical device handling application. The particular medical procedure can be associated with particular medical devices 102 that need be loaded into the medical device kit 100 for the particular procedure. It will be understood that medical device kits may be owned by a hospital or by another party or entity, and that medical device kits 100 may or may be not be identified by serial numbers. In an example configuration, the image sensor 88 of the wearable device 90 can identify a particular medical device kit by detecting its physical attributes when the medical device kit is in a field of view of the image sensor 88.

At 904, in accordance with the illustrated embodiment, the computer system determines at least one rule set corresponding to the identified medical device kit 100, and thus corresponding to the plurality of medical devices 102 configured to be stored in the medical device kit 100. The rule set can be retrieved from the database 30 based on the identifier of the medical device kit 100 and/or an identity of a medical procedure (e.g., a procedure code). In an example, the rule set can include rules pertaining to populating the medical device kit 100 with medical devices. For instance, the rule set can indicate a list of medical devices that are required to be loaded into the medical device kit 100 for a particular procedure. In an example, assembly of the medical device kit 100 is not complete until every medical device in the list of medical devices that are to be loaded into the medical kit 100 has been loaded into the medical device kit 100. Additionally, or alternatively, the medical device kit 100 can indicate a list of medical devices that are recommended to be loaded into the medical device kit 100. In an example, assembly of the medical device kit 100 can be completed without the medical devices that are listed as recommended being loaded into the medical device kit 100. Thus, the rule set can indicate which medical devices should be loaded into the medical device kit 100, but are not necessary to be loaded in order to complete a particular medical procedure. Further, the rule set can indicate a list of medical devices, and identify a respective storage location of the plurality of storage locations 106 that corresponds to each medical device in the list of medical devices. Such rules can guide the user or medical professional 22 in assembling the medical device kit 100.

By way of another example, the rule set can include rules specific to a particular medical device. For example, the rule set can include rules pertaining to physical abnormalities with a medical device, such as defects (e.g., manufacturing defects) with the medical device, or damage to the medical devices 102. The rule set can define a predetermined threshold associated with a physical characteristic of one or more medical devices. The physical characteristics can include at least one of size, shape, color, and so on. For instance, the predetermined threshold can stipulate permitted dimensions of a given medical device.

By way of yet another example, the rule set can include rules pertaining to cleanliness of a particular medical device. For example, a predetermined threshold can stipulate sterile requirements of a particular medical device. As another example, the rules can dictate that any medical device removed from the medical device kit 100 is determined to be unclean. As yet another example, the rule set may indicate that a given medical device has to have been sterilized within a time period stipulated by the predetermined threshold, in order for the given medical device to be loaded into the medical device kit 100 or used in a particular procedure.

At 906, physical characteristics of at least one of the medical device kit 100 and a medical device associated with the kit can be determined. In an example, the image sensor 88 of the wearable device 90 can detect physical characteristics of the medical device kit 100 when the medical device kit 100 is a field of view of the image sensor 88. For example, based one or more physical characteristics detected by the image sensor, the medical device handling application, and thus the computer system, can determine that there is no medical device at a given storage location, or that a medical device is stored at a given storage location. Additionally, or alternatively, the image sensor 88 of the wearable device 90 can detect physical characteristics of a medical device when the medical device is a field of view of the image sensor 88. For example, based one or more physical characteristics detected by the image sensor 88, the medical device handling application, and thus the computer system, can determine at least one of size, shape, and color of the medical device.

At 908, the medical device handling application, and thus the computer system, can compare the one or more physical characteristics of the at least one of the medical device kit 100 and the medical device to the rule set. By way of example, by determining the physical characteristics of the medical device kit 100, the computer system may determine that a given storage location is vacant. The rule set may identify a particular medical device that is required to be stored at the given storage location. Thus, by comparing the physical characteristics of the medical device kit to the rule set, the computer system can identify the medical device that corresponds to the given storage location.

By way of another example, by determining the physical characteristics of the medical device, the computer system may determine that the medical device is defective, damaged, disassembled, uncalibrated, and/or unclean. The physical characteristics can include at least one of size, shape, color, markings, and so on. The rule set may identify a predetermined threshold associated with a physical characteristic of the medical device. For instance, the predetermined threshold can stipulate permitted dimensions or cleanliness of a given medical device. If the physical characteristic is outside of the predetermined threshold, then the medical device can be determined to be defective, damage, and/or unclean.

At 910, the handling application, and thus the medical device computer system, can select a virtual object 150 to augment at least one of the medical device kit and the medical device based on comparing the one or more physical characteristics of the medical device kit 100 to the rule set. For example, if a given medical device is required to be assembled into the medical device kit 100, the computer system can select a virtual object that identifies the medical device. The selected virtual object may further indicate that the medical device is required. As another example, if the medical device is recommended to be assembled into the medical device kit 100, the computer system can select a virtual object that identifies the medical device. The selected virtual object can further indicate that the medical device is recommended. By way of further example, if the medical device is defective, damaged, or unclean, the computer system can select a virtual object that identifies the medical device. As described above, the virtual objects can include any graphics or text as desired. By way of example, a first virtual object can have a first color to indicate that a particular medical device is required, and a second virtual object can have a second color that is different than the first color to indicate that a particular medical device is recommended and not required.

In step 912, and with reference to FIG. 6B, the handling application, and thus the computer system, can insert a virtual object 150 into a view of the medical device kit 100, so as to generate the augmented view 152 of the medical device kit 100. Referring in particular to FIG. 6B, the display 107 can include translucent glass, and the display 107 can be worn by a user, such that the medical device kit 100 is configured to be viewed through the translucent glass, and virtual objects 150 can be displayed on the translucent glass. In alternative embodiments, the display 107 can be a screen that displays an image of the medical device kit 100 and virtual objects 150. As an example, the virtual objects 150 can include a first virtual object 150a that can include a graphic that identifies a medical device stored in the medical device that needs to be removed from the medical device kit. As another example, the virtual objects 150 can include a virtual object 150b that includes a graphic that identifies a first medical device 102 that corresponds to a first storage location 106a of the plurality of storage locations, so as to guide the user or medical professional 22 in assembling the medical device kit 100. The display 107 can be configured to superimpose the graphic over the view of the medical device kit, such that the graphic, and thus the virtual object 150b, is overlaid over the first storage location 106a. It will be understood that the graphics are not limited to the illustrated examples, and thus may be sized and shaped as desired.

In some cases, the computer system can identify the first medical device 102 that corresponds to the first storage location 106a, and can determine an inventory location of the first medical device 102. The inventory location can define where the first medical device 102 is stored in inventory, for instance in a hospital, an implant manufacturer, or elsewhere. The display 107 can be further configured to indicate the inventory location of the first medical device 102, so as to guide the user in retrieving the first medical device 102. In at least some embodiments, the computer system can determine whether the first medical device 102 is in stock in inventory or needs to be reordered. The display 107 can further be configured to indicate to the user whether or not the first medical device 102 is in stock. In at least some embodiments, the display 107 can provide the user the option of reordering the first medical device 102 in the event that the first medical device 102 is out of stock. In other embodiments, the display 107 can provide the user the option of notifying another medical professional, such as a doctor, that the medical device is out of stock. The medical professional can make a determination as to whether or not to delay the medical procedure based on the medical device being out of stock.

With continuing reference to FIG. 6B, the display 107 can include inputs, such as a touch screen for example, that provide the ability to control the computer system. Input may also be provided, for example, via other inputs of a computing device such as mouse, keyboard, camera, voice detection and the like. For example, the user can provide an input to confirm that the first medical device 102 has been loaded at the first storage location 106a. Alternatively, the image sensor 88 can detect that the first medical device 102 has been loaded at the first storage location 106a, for instance when the first storage location 106a, and thus the first medical device 102, is within a field of view of the image sensor 88. The computer system can be configured to display further information on the display 107 when an input is provided by a user. For example, the computer system can be configured to provide a location in inventory of a medical device in response to a user selecting a virtual object 150 associated with a medical device is missing from the medical device kit 100. As another example, the computer system can be configured to provide cleaning instructions when a user selects a medical device that has been identified as unclean by the computer system. As yet other examples, the computer system can be configured to provide instructions for assembling or disassembling the medical device, instructions for inspection of the medical device, instructions for calibration of the medical device, instructions for replacement of the medical device, or any combination of the above-mentioned instructions.

Thus, the medical device computer system can determine that the first medical device 102 has been loaded at the first storage location 106a. In response to determining that the first medical device 102 has been loaded at the first storage location 106a, the computer system can modify the virtual object 150a within the display 107. As one example, the computer system can modify the virtual object 150a by removing the virtual object 150 from the display 107, and thus from the view of the medical device kit 100. As another example, the computer system can change a color of the virtual object 150a to indicate that the first medical device 102 has been loaded correctly. Additionally, or alternatively, in response to determining that the first medical device 106a has been loaded at the first storage location 106a, the computer system can select another virtual object 150b to augment the medical device kit 100, and insert the virtual object into the view of the medical device kit 100 so as to generate another augmented view of the medical device kit 100.

Selections can be made by users via a variety of mechanisms including, for example, inputs provided by user interface 86 of the example computing device 78. For instance, users can select a given medical device that the user intends to load via a touch-screen display, such as the display 107 for example, by touching a portion of the display 107. Alternatively, users can use a mouse or keyboard to provide inputs and selections to the medical device handling application. Alternatively still, the image sensor 88 can identify a medical device that the user intends to load into medical device kit 100 when the given medical device is within a field of view of the image sensor 88. Yet still, the image sensor 88 can be configured to recognize hand motions pertaining to a section made by a user. In an example configuration, in response to receiving an identity of a medical device that the user or medical professional 22 intends to load into the medical device kit 100, the computer system can insert one or more virtual objects 150c into the augmented view 152 of the medical device kit. The virtual objects 150c can indicate one or more acceptable storage locations 106c for the medical device that the user intends to load into the medical device kit 100. The virtual objects 150c can be superimposed over the physical view of the storage locations 106c. After the medical device, for instance medical screws 108, are stored at the storage locations 106c, the computer system can remove the virtual objects 150c from the augmented view 152 or modify an appearance of the virtual objects 150c in a manner similar to that described above. Further, the computer system can suggest a next medical device or next surgical step, and the computer system can repeat one or more of steps 902 to 912 for the next medical device or next surgical step.

It will be understood that any number of augmented views of the medical device kit, and of the medical devices, can be generated and displayed. For example, a virtual object 150 can be inserted into the view of the medical device kit when the medical device kit is assembled, to indicate that assembly is complete, thereby also indicating that the medical device kit can be moved to an operating room or elsewhere.

The plurality of storage locations 106 can be configured to store a plurality of medical devices as described above, such as sterile or nonsterile medical screws, medical plates, other medical implants, other medical devices configured to be attached or fixated to a patient, other assorted medical devices, or any combination thereof. For instance, in accordance with the example illustration, the storage locations 106 can define recesses or holes 106c that are sized so as to receive at least a portion of select medical devices 102 so as to secure the medical devices 102 within the storage object 100, although it will be understood that the storage locations 106 can be alternatively shaped as desired.

As described above, the image sensor 88 of the wearable device 90 can be configured to identify medical devices 102. For instance, a given medical device can be identified by a medical device identifier. A medical device identifier may be, for example, a unique identifier. However, it is not required that a medical device identifier must be a unique identifier. In some cases, a medical device identifier may be, for example, a global trade identification number (GTIN). A medical device identifier can, for example, be scanned from a bar code. A medical device identifier can also, for example, be disposed on a label of a package that contains a corresponding medical device 102. As another example, a medical device identifier can be etched or otherwise directly disposed on a corresponding medical device 102. It will be understood that a medical device identifier can be alternatively provided to the computer system as desired.

The image sensor 88 can be configured to generate a detection of the plurality of medical devices 102 when each medical device is within a field of view of the image sensor 88, so as to determine a respective identity of the respective medical device, or the identity may be otherwise received by the computer system. In an example, the image sensor 88 can detect the medical device identifier. Based on the respective identity of the plurality of medical devices, the computer system can retrieve data associated with each medical device 102. Further, the display 107 can be configured to render the data associated with each medical device, so as to guide utilization of each medical device. Example data includes, without limitation, model and make of the medical device, medical procedures for the medical device, instructions for loading or using the medical device in various procedures, and locations in inventory of the medical device.

Based on the detection of one or more medical devices 102, the medical device computer system can determine one or more characteristics or attributes of the one or more medical devices 102. The computer system can further determine a rule, for instance multiple rules, corresponding to at least one of the detected medical devices. The computer system can compare the one or more characteristics of a given medical device to the rule associated with the given medical device. Based on the comparison of the one or more characteristics of the medical device to the rule set corresponding to the medical device, the medical device computer system can identify an anomaly such as a flaw, defect, damage, or contamination associated with the medical device. Further, the computer system can be configured to insert a virtual indication of the anomaly into a view of the medical device, so as to generate an augmented view of the medical device. Identifying the anomaly can include determining that one or more characteristics of the medical device are outside the predetermined threshold. By way of example, the predetermined threshold can relate to physical dimensions or attributes of the medical device. By way of further example, the predetermined threshold can relate to a status of the medical device, for instance an age of the medical device, a calibration status of the medical device, or a sterilization status of the medical device. In an example configuration, if a given medical device has not been sterilized within an appropriate time period, such that its sterilization status falls outside of a predetermined sterilization threshold, the computer system can render, for instance display or provide audio, cleaning instructions. Thus, cleaning instructions can be rendered on the display in response to identifying an anomaly. The cleaning instructions can be rendered on the display such that, when the cleaning instructions are performed, the anomaly is removed. The cleaning instructions can be rendered as, for example, text instructions, image instructions, video instructions, or any combination thereof.

With general reference to FIGS. 6A and 6B, different virtual objects 150 can be inserted into views of the medical device kit 100 or the medical devices 102 in different settings. In some cases, virtual objects 150 that indicate which medical devices should be stored in which storage locations 106 are inserted to augment medical device kits 100 in a storage/inventory type of setting, while virtual objects 150 that indicate flaws or defects in a medical device can be inserted to augment medical devices 102 in a storage/inventor type of setting or in an operating room or other type of patient-procedure setting. For example, the medical storage kit 100 and the wearable device 90 can be physically moved from a storage/inventory area into an operating room.

In accordance with an example embodiment, image sensor 88 can detect that a particular medical device 102 is removed from the medical device kit 100. The image sensor 88 can additionally, or alternatively, detect that a particular medical device 102 is used on a patient (such as, for example, in an operating room or another patient-procedure setting). In some embodiments, the computer system can determine whether a particular medical device 102 is unclean or de-sterilized based on the medical device 102 being removed from the medical device kit 100 and/or being used on a particular patient.

By detecting use on a patient, the computer system can identify a particular medical device 102 that is being used on a particular patient so that, for example, the medical device 102 can be tracked after use on the patient. Accordingly, a patient identifier can be input into the computer system so as to be received by the computer system. Such a patient identifier may include, for example, a name, address, insurance information and/or social security number. Information that is received by the computer system, and thus information that can be stored by the computer system, can also include, for example, an indication of a time, date, location, hospital, doctor, and other staff that may be associated with an implantation, attachment, or other use of the medical device on the patient.

As should be appreciated, some or all of the steps depicted in FIG. 9 may be repeated any number of times when, for example, additional medical devices are stored in and/or removed from the medical device kit 100. There is no requirement that only a single medical device can be stored at any particular storage location. For example, in some cases, multiple medical devices may be stored at a particular storage location. Also, there is no requirement that a particular medical device must occupy only a single storage location. For example, in some cases, a particular medical device may occupy or otherwise be stored at multiple storage locations. In such cases, for example, the virtual objects inserted into the view of the medical device kit 100 can indicate that a particular medical device can be stored in multiple storage locations, or that multiple medical devices can be stored at a given storage location.

By way of example, if the medical device kit 100 is dropped or the medical devices 102 stored within the medical device kit 100 are otherwise mixed together, the medical device handling application can display a virtual object that indicates that the inventory within the medical device kit 100 has been mixed, so as guide the user in reassembling the medical device kit 100.

In an embodiment, a method of handling medical devices 102 associated with the medical device kit 100 can be performed by one or more medical device handling applications, which can be installed on a computer system that includes one or computing devices such as a tablet computer, desktop computer, laptop, or mobile phone, without the use of a head-mounted display. Initially, a medical device kit, for instance the medical device kit 100, is identified as in step 902 of FIG. 9. In an example, the medical device kit 100 can include an identifier, such as a serial number for instance. The identifier can include a code, for instance a QR code, that can be scanned by the image sensor 88, or the identifier can be alternatively entered into the medical device handling application. The identifier of the medical device kit 100 can be associated with a particular medical procedure corresponding to a particular patient. Additionally, or alternatively, a particular medical procedure, such as a procedure code or patient name for the procedure, can be entered or scanned into the medical device handling application. The particular medical procedure can be associated with particular medical devices 102 associated with the medical device kit 100 for the particular procedure.

After identifying the medical device kit 100, the computer system determines at least one information set corresponding to the identified medical device kit 100, and thus corresponding to the plurality of medical devices 102 configured to be stored in the medical device kit 100. The information set can be retrieved from the database 30 based on the identifier of the medical device kit 100 and/or an identity of a medical procedure (e.g., a procedure code). The information set can include information pertaining to each of the medical devices 102 associated with the medical device kit 100. For example, the information can include at least one, up to all, of information pertaining to whether each instrument is defective, has been damaged, and has been used. Additionally, or alternatively, the information set can include instructions for cleaning (e.g., sterilizing) each of the medical devices 102.

After determining the at least one information set, the handling application, and thus the computer system, can select at least one virtual object 150 to display on a screen of the computer system. For example, the handling application can select a list of medical devices 102 of the medical device kit 100 to display on the screen, and the screen can display the list. Additionally, or alternatively, the handling application can select at least one virtual representation of each medical device 102 associated with the medical device kit 100 to display on the screen, and the screen can display the at least one virtual representation.

Upon displaying the at least one virtual object 150, the user or medical professional can select a virtual object 150 corresponding to one of the medical devices 102. In response, the handling application can display the information about the medical device 102 on a screen of the computer system. Optionally, the handling application can provide the user or health care professional an option to update the information. For example, the user or health care professional can update at least one, up to all, of information pertaining to whether the instrument is defective, has been damaged, and has been used.

Additionally, or alternatively, in response to selecting a virtual object 150, the medical device handling application can provide instructions for cleaning (e.g., sterilizing) the medical device 102 on the screen of the computer system. The cleaning instructions can be rendered as, for example, text instructions, image instructions, video instructions, or any combination thereof. After selecting a virtual object 150 for a medical device 102, the user can select a subsequent virtual object 150 corresponding to subsequent one of the medical devices 102, and this process can be repeated to update the information of each medical device 102 in the medical device kit 100 and/or to clean each medical device 102 in the medical device kit 100.

While example embodiments of devices for executing the disclosed techniques are described herein, the underlying concepts can be applied to any computing device, processor, or system capable of communicating and presenting information as described herein. The various techniques described herein can be implemented in connection with hardware or software or, where appropriate, with a combination of both. Thus, the methods and apparatuses described herein can be implemented, or certain aspects or portions thereof, can take the form of program code (i.e., instructions) embodied in tangible non-transitory storage media, such as floppy diskettes, CD-ROMs, hard drives, or any other machine-readable storage medium (computer-readable storage medium), wherein, when the program code is loaded into and executed by a machine, such as a computer, the machine becomes an apparatus for performing the techniques described herein. In the case of program code execution on programmable computers, the computing device will generally include a processor, a storage medium readable by the processor (including volatile and non-volatile memory and/or storage elements), at least one input device, and at least one output device, for instance a display. The display can be configured to display visual information. For instance, the displayed visual information can include a storage object image representative of a storage object, wherein the storage object image includes a plurality of storage location areas that represent a plurality of storage locations within the storage object. The program(s) can be implemented in assembly or machine language, if desired. The language can be a compiled or interpreted language, and combined with hardware implementations.

The techniques described herein also can be practiced via communications embodied in the form of program code that is transmitted over some transmission medium, such as over electrical wiring or cabling, through fiber optics, or via any other form of transmission. When implemented on a general-purpose processor, the program code combines with the processor to provide a unique apparatus that operates to invoke the functionality described herein. Additionally, any storage techniques used in connection with the techniques described herein can invariably be a combination of hardware and software.

While the techniques described herein can be implemented and have been described in connection with the various embodiments of the various figures, it is to be understood that other similar embodiments can be used or modifications and additions can be made to the described embodiments without deviating therefrom. For example, it should be appreciated that the steps disclosed above can be performed in the order set forth above, or in any other order as desired. Further, one skilled in the art will recognize that the techniques described in the present application may apply to any environment, whether wired or wireless, and may be applied to any number of such devices connected via a communications network and interacting across the network. Therefore, the techniques described herein should not be limited to any single embodiment, but rather should be construed in breadth and scope in accordance with the appended claims.

What is claimed:

1. A medical device computer system comprising:
   a processor;
   a display configured to display virtual objects along with a view of a medical device kit, the medical device kit including a plurality of storage locations each corresponding to a respective one of a plurality of medical devices, such that the plurality of storage locations are each configured to store a respective medical device;
   an image sensor in communication with the processor, the image sensor configured to detect one or more physical characteristics of at least one of the medical device kit and the plurality of medical devices, the one or more physical characteristics including a geometrical dimension of a first one of the plurality of medical devices; and
   at least one memory having stored therein instructions that, upon execution by the processor, cause the computer system to perform operations comprising:
      determining a rule set corresponding to the at least one of the medical device kit and the plurality of medical devices;
      comparing the one or more physical characteristics of the first one of the plurality of medical devices to the rule set;
      determining, based on the one or more physical characteristics detected by the image sensor, that an incorrect medical device is at a first storage location of the plurality of storage locations;
      selecting, based on the comparing the one or more physical characteristics to the rule set, a first virtual object to augment the view of the medical device kit indicating that the incorrect medical device is at the first storage location;
      inserting the first virtual object into the view of the medical device kit so as to generate a first augmented view;
      after the inserting step, generating a second virtual object that includes instructions that guide the retrieval of a correct first one of the plurality of medical devices from inventory, and overlaying the instructions over the first storage location;
      determining that the first one of the plurality of medical devices has been loaded at the first storage location and is correct and, in response to determining that the first medical device loaded at the first storage location is correct, modifying the first virtual object within the view of the medical device kit, wherein the first virtual object indicates that the first one of the plurality of medical devices is required for a medical procedure;
      comparing the geometrical dimension of the first one of the plurality of medical devices to a threshold;
      displaying a virtual indication that the geometrical dimension of the first one of the plurality of medical devices is outside of the threshold;
      comparing the one or more physical characteristics of a second one of the plurality of medical devices to the rule set;
      selecting, based on the comparing the one or more physical characteristics to the rule set, a third virtual object to augment the view of the medical device kit; and
      inserting the third virtual object into the view of the medical device kit so as to generate a second augmented view, wherein the third virtual object is different from the first virtual object and the third virtual object indicates that the second one of the plurality of medical devices is optional for the medical procedure.

2. The computer system as recited in claim 1, wherein the display comprises translucent glass, and the display is configured to be worn by a user, such that the medical device kit is configured to be viewed through the translucent glass, and the first virtual object is configured to be displayed on the translucent glass.

3. The computer system as recited in claim 1, wherein the first virtual object comprises a graphic that identifies a medical device stored in the medical device kit that needs to be removed from the medical device kit.

4. The computer system as recited in claim 1, wherein the first virtual object comprises a graphic that identifies a first medical device that corresponds to a first storage location of the plurality of storage locations, so as to guide a user in assembling the medical device kit.

5. The computer system as recited in claim 4, wherein the display is configured to superimpose the graphic over the view of the medical device kit, such that the graphic is overlaid over the first storage location.

6. The computer system as recited in claim 1, wherein the at least one memory has stored therein instructions that, upon execution by the processor, cause the computer system to perform operations comprising:
    identifying the first medical device that corresponds to the first storage location; and
    determining an inventory location of the first medical device, the inventory location defining a location of the first medical device in inventory,
    wherein the display is configured to indicate the inventory location of the first medical device.

7. The computer system as recited in claim 1, the at least one memory having stored therein instructions that, upon execution by the processor, cause the computer system to perform operations comprising:
    determining that the first medical device has been loaded at the first storage location; and
    in response to determining that the first medical device has been loaded at the first storage location, modifying the first virtual object within the view of the medical device kit.

8. The computer system as recited in claim 1, wherein the image sensor is configured to generate a detection of the medical devices when each medical device is within a field of view of the image sensor so as to determine a respective identity of the respective medical device, and the at least one memory has stored therein instructions that, upon execution by the processor, cause the computer system to perform operations comprising:
    based on the respective identity of the medical devices, retrieve data associated with each medical device.

9. The computer system as recited in claim 8, wherein the display is configured to render the data associated with each medical device, so as to guide utilization of each respective medical device.

10. The computer system as recited in claim 8, wherein the at least one memory has stored therein instructions that, upon execution by the processor, cause the computer system to perform operations comprising:
    determining, based on the detection of at least one medical device of the medical devices, one or more characteristics of the at least one medical device;
    determining a rule corresponding to the at least one medical device;
    comparing the one or more characteristics of the at least one medical device to the rule;
    identifying, based on the comparing of the one or more characteristics of the at least one medical device to the rule corresponding to the at least one medical device, an anomaly associated with the at least one medical device; and
    inserting a virtual indication of the anomaly into a view of the at least one medical device so as to generate an augmented view.

11. The computer system as recited in claim 10, wherein the rule set defines a predetermined threshold associated with a physical characteristic of the at least one medical device.

12. The computer system as recited in claim 11, wherein identifying the anomaly comprises determining that the one or more characteristics of the at least one medical device are outside the predetermined threshold.

13. The computer system as recited in claim 11, wherein the at least one memory has stored therein instructions that, upon execution by the processor, cause the computer system to perform operations comprising:
    rendering, in response to identifying the anomaly, cleaning instructions on the display such that, when the cleaning instructions are performed, the anomaly is removed.

14. The computer system as recited in claim 1, wherein the rule set indicates a list of medical devices to be loaded into the medical device kit.

15. The computer system as recited in claim 1, wherein the rule set indicates a list of medical devices, and identifies a respective storage location within the medical device kit for each medical device in the list of medical devices.

16. A computer-implemented method of guiding a user in handling a plurality of medical devices associated with a medical device kit, the method comprising:
    detecting one or more physical characteristics of at least one of the medical device kit and the plurality of medical devices of the medical device kit, the one or more physical characteristics including a geometrical dimension of a first one of the plurality of medical devices;
    determining a rule set corresponding to the at least one of the medical device kit and the plurality of medical devices;
    comparing the one or more physical characteristics of the first one of the plurality of medical devices to the rule set;
    determining, based on the one or more physical characteristics detected by the image sensor, that an incorrect medical device is at a first storage location of the medical device kit among a plurality of storage locations that are each configured to receive a respective medical device;
    selecting, based on the comparing the one or more physical characteristics to the rule set, a first virtual object to augment a view of the medical device kit;
    inserting the first virtual object into the view of the medical device kit so as to generate a first augmented view;
    after the inserting step, generating a second virtual object that includes instructions that guide the retrieval of a correct the first one of the plurality of medical devices from inventory, and overlaying the instructions over the first storage location;
    determining that the first one of the plurality of medical devices has been loaded at the first storage location and is correct and, in response to determining that the first medical device loaded at the first storage location is correct, modifying the first virtual object within the view of the medical device kit, wherein the first virtual object indicates that the first one of the plurality of medical devices is required for a medical procedure;
    comparing the geometrical dimension of the first one of the plurality of medical devices to a threshold;
    displaying a virtual indication that the geometrical dimension of the first one of the plurality of medical devices is outside of the threshold;
    comparing the one or more physical characteristics of a second one of the plurality of medical devices to the rule set;

selecting, based on the comparing the one or more physical characteristics to the rule set, a third virtual object to augment the view of the medical device kit; and inserting the third virtual object into the view of the medical device kit so as to generate a second augmented view, wherein the third virtual object is different from the first virtual object and the third virtual object indicates that the second one of the plurality of medical devices is optional for the medical procedure.

17. The computer-implemented method of claim 16, wherein the first augmented view identifies the storage location within the medical device kit and at least one of the medical devices that is to be loaded at the storage location, so as to guide a user in assembling the medical device kit.

18. The computer-implemented method of claim 16, comprising:

identifying, based on the comparing of the one or more characteristics, a defect associated with the at least one medical device; and inserting a virtual indication of the defect into a view of the at least one medical device so as to generate the first augmented view.

\* \* \* \* \*